(12) United States Patent
Anderson (10) Patent No.: US 6,705,320 B1
(45) Date of Patent: Mar. 16, 2004

(54) METHODS FOR PERFORMING TRACHEAL INTUBATION ON AN ANIMAL AND ENDOTRACHEAL TUBES THEREFORE

(76) Inventor: Scott M. Anderson, 821 Toyopa Dr., Pacific Palisades, CA (US) 90272

( * ) Notice: Subject to any disclaimer, the term of this patent is extended or adjusted under 35 U.S.C. 154(b) by 0 days.

(21) Appl. No.: 10/326,940

(22) Filed: Dec. 23, 2002

(51) Int. Cl.⁷ .................. A61M 16/00; A61M 31/00
(52) U.S. Cl. .................. 128/207.14; 604/103.08
(58) Field of Search .......... 128/200.24, 207.14–207.16, 128/207.12; 604/97.01–97.03, 98.02, 99.01–99.03, 915, 916, 920, 96.01, 103.08, 103.06; 600/561

(56) References Cited

U.S. PATENT DOCUMENTS

| | | | | | |
|---|---|---|---|---|---|
| 3,363,629 A | * | 1/1968 | Kuhn | .................. | 128/207.15 |
| 3,659,611 A | * | 5/1972 | Miller | .................. | 128/207.15 |
| 3,810,474 A | * | 5/1974 | Cross | .................. | 128/207.15 |
| 4,018,231 A | * | 4/1977 | Wallace | .................. | 128/207.15 |
| 4,178,939 A | * | 12/1979 | Stephens | .................. | 128/207.15 |
| 4,185,638 A | * | 1/1980 | Bruner | .................. | 604/100.01 |
| 4,340,046 A | * | 7/1982 | Cox | .................. | 128/207.17 |
| 5,062,423 A | * | 11/1991 | Matson et al. | .................. | 128/207.15 |
| 5,218,970 A | * | 6/1993 | Turnbull et al. | .................. | 600/561 |
| 5,318,021 A | * | 6/1994 | Alessi | .................. | 128/207.15 |
| 5,333,608 A | * | 8/1994 | Cummins | .................. | 128/207.14 |
| 5,494,029 A | * | 2/1996 | Lane et al. | .................. | 128/207.15 |
| 5,546,936 A | * | 8/1996 | Virag et al. | .................. | 128/207.14 |
| 5,590,647 A | * | 1/1997 | Nye | .................. | 128/207.14 |
| 5,720,726 A | * | 2/1998 | Marcadis et al. | .................. | 604/103.08 |
| 5,765,559 A | * | 6/1998 | Kim | .................. | 128/207.15 |
| 6,530,898 B1 | * | 3/2003 | Nimkar et al. | .................. | 604/97.03 |
| 6,651,664 B1 | * | 11/2003 | Lomholt | .................. | 128/207.14 |
| 2002/0157665 A1 | * | 10/2002 | Igarashi et al. | .................. | 128/200.22 |
| 2002/0195103 A1 | * | 12/2002 | O'Mara | .................. | 128/200.26 |

FOREIGN PATENT DOCUMENTS

| | | | |
|---|---|---|---|
| EP | 1062964 | * | 12/2000 |
| JP | 10/243950 | * | 9/1998 |
| JP | 10/234753 | * | 10/1998 |

* cited by examiner

*Primary Examiner*—Aaron J. Lewis
*Assistant Examiner*—Teena Mitchell
(74) *Attorney, Agent, or Firm*—Timothy Thut Tyson; Ted Masters; Freilich, Hornbaker & Rosen (57) ABSTRACT

Methods for performing tracheal intubation of small animals are shown utilizing an endotracheal tube specifically designed for them. The endotracheal tube has a zigzag bend and a distal portion having an outwardly facing surface. The outwardly facing surface is used to depress the epiglottis of the animal thereby giving a doctor a clear view of the animal's trachea. The endotracheal tube also includes a tapered end which is easily inserted between the arytenoid cartilages of the larynx, and a pressure sensor which provides a quantitative indication of the air pressure within the cuff of the endotracheal tube.

10 Claims, 7 Drawing Sheets

METHODS FOR PERFORMING TRACHEAL INTUBATION ON AN ANIMAL AND ENDOTRACHEAL TUBES THEREFORE

TECHNICAL FIELD

The present invention pertains generally to tracheal intubation, and more particularly to methods and apparatus for performing tracheal intubation on animals.

BACKGROUND OF THE INVENTION

Tracheal intubation is commonly used in human patients during medical procedures in order to keep air passing into the lungs and to prevent foreign matter from entering the lungs. An endotracheal tube typically made from polyvinyl chloride, rubber, silicone, or the like is inserted into the trachea. A cuff on the tube is then inflated until the cuff seals off the trachea leaving only the endotracheal tube as the source of air to the lungs. As air is injected, an external pilot balloon also inflates thereby giving the doctor a subjective indication of the degree of cuff inflation.

Methods and devices for tracheal intubation are well known in the art. For example, U.S. Pat. No. 4,850,371 shows a non-invasive apparatus for continuously measuring the cardiac output and cardio-respiratory function including a gas sampling device which is inserted into the mouth of a human subject. The gas sampling device may be a disposable endotracheal tube or a smaller disposable mouthpiece. Each of these gas sampling devices is provided with a plurality of passages for sampling the lung gases and for continuously sampling the gas pressure on opposite sides of a capillary restriction member. A miniature motor pump mass spectrometer module is mounted on the upper end of the endotracheal tube or mouthpiece. Electronic circuitry connected to the mass spectrometer permits constant visual monitoring of the cardiac output and cardio-respiratory function.

U.S. Pat. No. 4,879,999 illustrates an endotracheal device provided with a calorimetric carbon dioxide indicator. The device functions to indicate the proper intratracheal placement of an endotracheal tube by detecting for the presence of carbon dioxide in expired air passing through the device.

U.S. Pat. No. 4,976,261 discloses an endotracheal tube for artificial ventilation which employs a primary cuff and a secondary cuff for locating and positioning the tube in the trachea of a patient. The secondary cuff employs a balloon sleeve which is located near the distal end of the tube. The secondary balloon sleeve is sealed against the tube in a reverse folded configuration. The tube wall includes a number of lumens which may be employed for various auxiliary functions.

U.S. Pat. No. 5,285,778 comprises an endotracheal tube having a main tube having a proximal end portion, distal end portion, and an inflatable annular cuff disposed on the main tube in sealed relation thereto adjacent to the distal end portion. An inflation tube extends from the distal end portion into the cuff. A viewing lens is located on the distal end portion and is optically coupled to a first optical fiber extending from the proximal end portion to the distal end portion. A viewing device is attached to a proximal end of the first optical fiber. An illumination port is located on the distal end portion coupled to a second optical fiber extending from the proximal end portion to the distal end portion. An illumination source is optically coupled to a proximal end of the second optical fiber. The extended insertion of the endotracheal tube and conditions of adjacent tissue can be viewed by means of the viewing device. A flushing tube extends from a flushing source adjacent the proximal end portion to a flushing outlet port located at the distal end portion adjacent the viewing lens for flushing mucous away from the viewing lens. In one embodiment, an auxiliary tube extends through a sealable port in a wall of the proximal end portion and slides through the sealable port, through the main tube, and out of the distal end portion. The auxiliary tube includes fiber optic illumination and viewing elements on a distal end portion and an inflatable annular cuff on the distal end portion.

U.S. Pat. No. 5,421,325 consists of an endotracheal assembly having an endotracheal tube, a malleable obturator inside the tube for enabling a placement of a distal end of the tube into a patient's trachea, and a pressure-sensitive detector mounted to the obturator at the distal end. The purpose of the detector is to sense air or gas pressure above a predetermined threshold exerted against a distal end of the obturator upon placement of the tube with the obturator into the patient. Upon an initial insertion of the tube and the obturator into a patient's trachea and possible manipulation of the tube and the obturator to effectuate a placement of the tube, a compressive pressure is exerted externally on the patient's chest. The compressive pressure forces air out of the patient's lungs and, if the tube and obturator assembly is properly placed, effectuates a change in the condition of the pressure sensor. That change in condition indicates that pressure above a predetermined level was exerted against the detector element.

U.S. Pat. No. 5,954,636 describes apparatus and method for selectively blocking respiratory airflow to a pediatric lung or a single lobe of the lung. The apparatus comprises an endotracheal tube providing a passage for a bronchoscope and a second flexible tube which is attached to the endotracheal tube. A bronchial blocker assembly, having a pair of axial passageways, is insertable into the second flexible tube. A stylet is inserted into one of the axial passageways to guide the endotracheal tube and bronchial blocker assembly along a pediatric patient's windpipe. Means are provided for fixing the bronchial blocker assembly relative to the second axial passageway when the bronchial blocker assembly is in place.

Currently, endotracheal tubes used for dogs and cats are not veterinary specific. Instead, tubes designed for humans are used resulting in numerous problems. Small patients such as dogs and cats in particular are difficult to intubate since the opening of the larynx is obscured by the tongue base and is therefore difficult to see. Furthermore, laryngospasm, which is spastic closure of the larynx, occurs when the tube tip touches the larynx. It is usually necessary to apply topical anesthetic to minimize laryngospasm. Also, since the distal end of a typical endotracheal tube is relatively blunt, a narrow diameter stylet is placed in the lumen of the tube and passed into the opening of the larynx to force it slightly open. The endotracheal tube is then slid along the stylet to achieve intubation. Use of a stylet can potentially traumatize the trachea. Additionally, a larnygoscope is usually needed to force the epiglottis down, see the laryngeal opening, and verify that the tube has been placed in the larynx rather than the esophagus. Erroneous placement of the endotracheal tube in the esophagus is a major cause of anesthetic death and disability. Also, the inflation pressure within the cuff is critical. Insufficient inflation can allow saliva, vomit, or other foreign matter to seep into the lungs, with potentially fatal consequences. Conversely, excessive pressure in the cuff can rupture the trachea, or damage the tracheal lining, particularity in the case of cats. Current pilot balloons offer only subjective means of judging cuff inflation pressure In view of problems discussed above, a need exists for an endotracheal tube specifically designed for use on small animals which eliminates the problems associated with using tubes designed for humans.

SUMMARY OF THE INVENTION

The present invention is directed to methods of tracheal intubation and associated endotracheal tubes specifically designed for animals. The endotracheal tube is angled in zigzag fashion so as to force the epiglottis down during intubation and provide better visibility of the trachea. The endotracheal tube also includes a tapered pointed end which serves as an integrated stylet. The tapered end allows the tube to pass more easily between the arytenoid cartilages of the larynx during laryngospasm. This eliminates the need for a separate stylet. The endotracheal tube further includes a quantitative pressure sensor for determining the pressure within the inflatable cuff, thereby preventing both over inflation and under inflation.

In accordance with a preferred embodiment of the invention, a method for performing tracheal intubation on an animal, includes:

(a) providing an animal having a mouth and an epiglottis;

(b) providing an endotracheal tube having:
   an elongated firm body having a proximal portion and a distal portion;
   a double bend disposed in the body between the proximal and distal portions, so that the distal portion is transversely displaced with respect to the proximal portion; and,
   the distal portion having an outward facing surface for depressing the epiglottis of the animal;

(c) inserting the distal end of the endotracheal tube into the mouth of the animal; and, (d) using the outward facing surface to depress the epiglottis of the animal.

Another preferred method for performing tracheal intubation on an animal includes:

(a) providing an animal having a larynx having arytenoid cartilages and a trachea;

(b) providing an endotracheal tube having:
   an elongated body having a proximal portion and a distal portion;
   the distal portion having a tapered end for passing the endotracheal tube through the arytenoid cartilages and into the trachea; and,
   the tapered end forming an angle which is less than 25°; and, (c) using the tapered end to pass the endotracheal tube through the arytenoid cartilages and into the trachea of the animal.

Another preferred method for performing tracheal intubation on an animal includes:

(a) providing an animal having a trachea;

(b) providing an endotracheal tube including:
   an inflatable cuff;
   a pilot balloon connected to the cuff; and,
   a pilot balloon including a pressure indicator for measuring air pressure within the cuff;

(c) inserting the cuff into the trachea of animal;

(d) inflating the inflatable cuff; and, (h) using the pressure indicator to measure air pressure within the cuff.

Other aspects of the present invention will become apparent from the following detailed description, taken in conjunction with the accompanying drawings, which illustrate, by way of example, the principles of the invention.

DETAILED DESCRIPTION OF THE INVENTION

Figure 1:
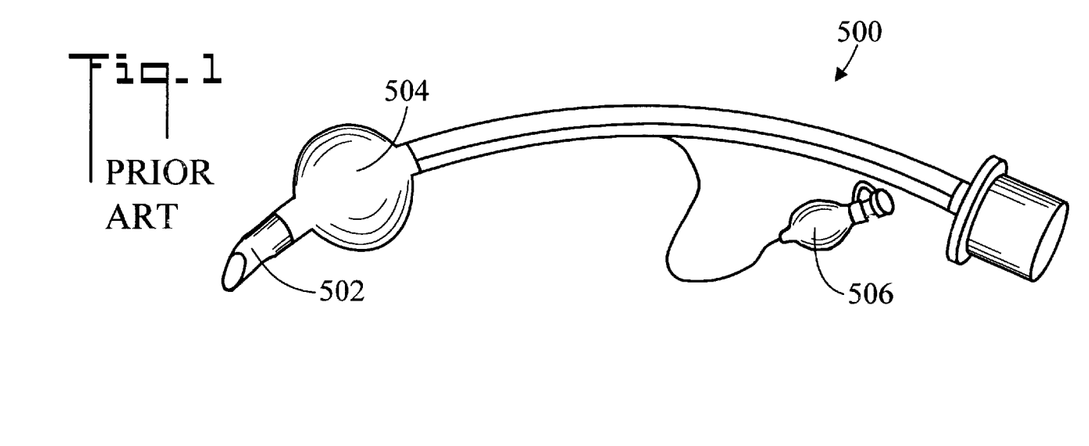
FIG. 1 is a perspective view of a prior art endotracheal tube used on humans.

Referring initially to FIG. 1, there is illustrated a perspective view of a prior art endotracheal tube used on humans, generally designated as 500. Endotracheal tube 500 includes a blunt tip 502, an inflatable cuff 504 shown in an inflated condition, and a pilot balloon 506. Endotracheal tube 500 is inserted into the mouth of a patient so that cuff 504 resides in the patient's trachea. Once in place, air is injected through a valve into a small diameter tube leading to cuff 504 until the cuff expands and seals off the trachea leaving only the endotracheal tube 500 as a source of air to the lungs. Pilot balloon 506 is connected to cuff 504 by a small tube. The degree of distension of the pilot balloon 506 allows the doctor to subjectively estimate whether cuff 504 is sufficiently inflated. Endotracheal tube 500 is typically fabricated from flexible materials such as polyvinyl chloride, rubber, silicone, and the like.

Figure 2:
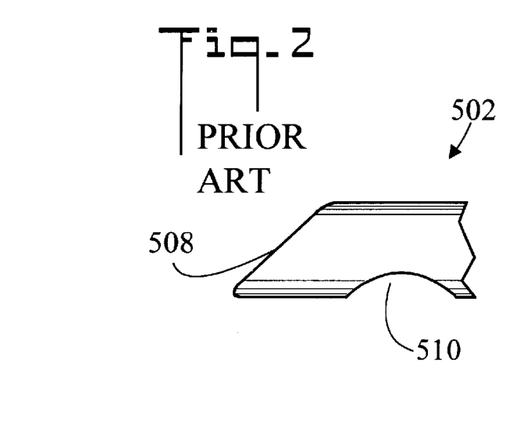
FIG. 2 is an enlarged side elevation view of a prior art blunt tip.
Figure 3:
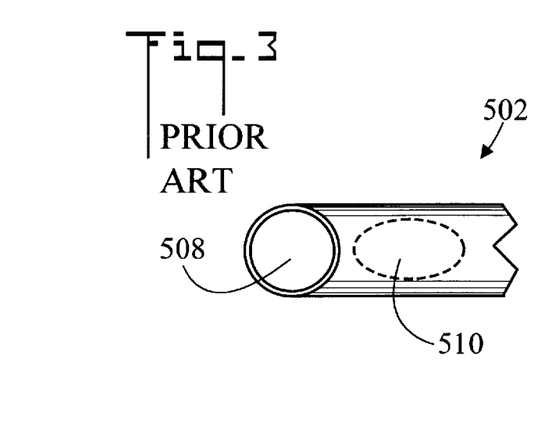
FIG. 3 is an enlarged top elevation view of the prior art blunt tip.

FIGS. 2 and 3 are enlarged side elevation and top plan views, respectively, of prior art blunt tip 502. Blunt tip 502 has an open end 508 which is cut at about a 40° angle. Blunt tip 502 further includes a side hole 510 known as "Murphy's eye" which supplements open end 508 as an air passage.

Figure 4:
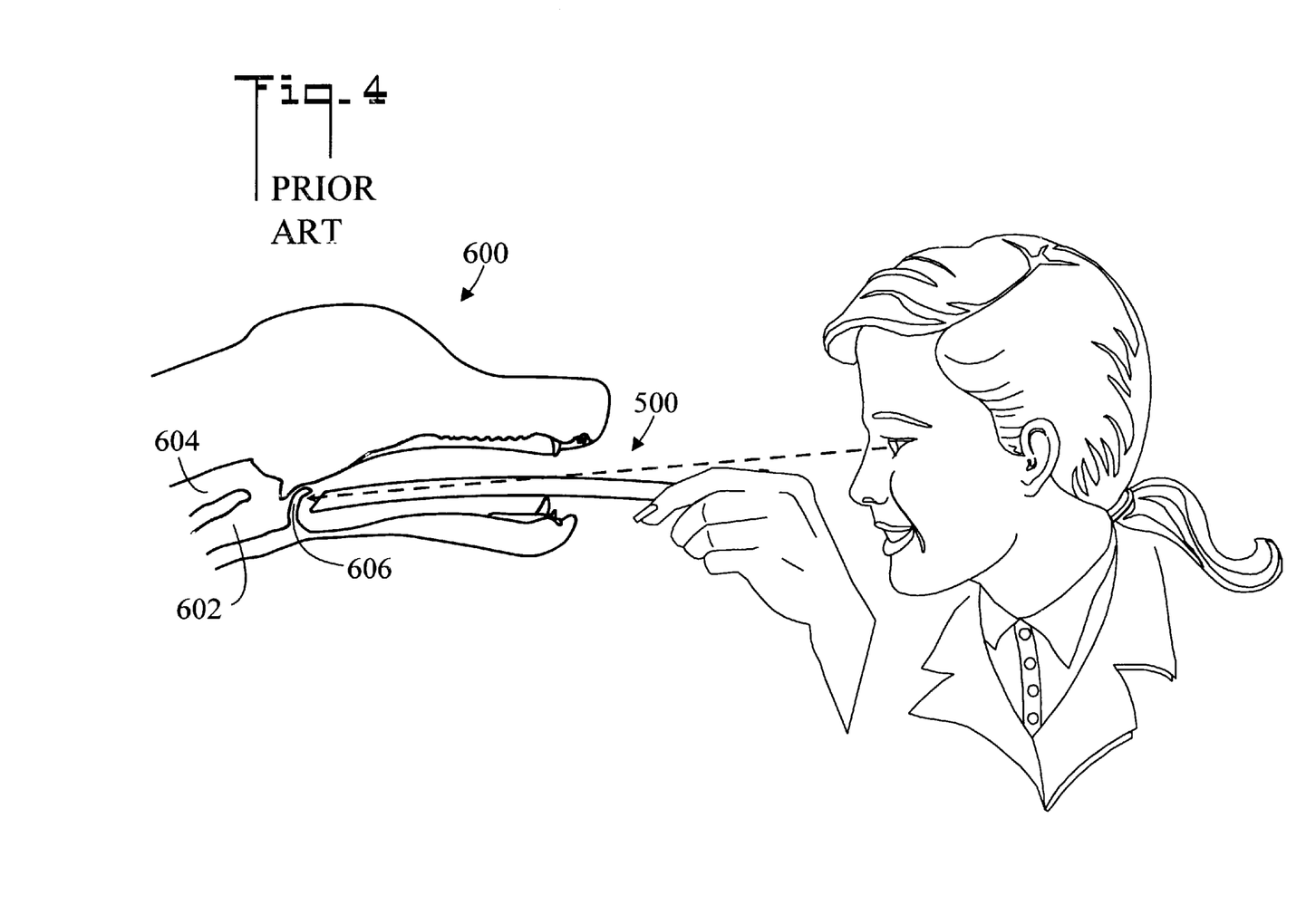
FIG. 4 is a reduced side elevation view of the prior art endotracheal tube being inserted into the mouth of an animal, such as a dog or cat.

FIG. 4 is a reduced side elevation view of prior art endotracheal tube 500 being inserted into the mouth of an animal 600, such as a dog or cat. The animal has a trachea 602, an esophagus 604, and an epiglottis 606. It is noted that epiglottis 606 blocks the doctor's view of the trachea 602.

Figure 5:
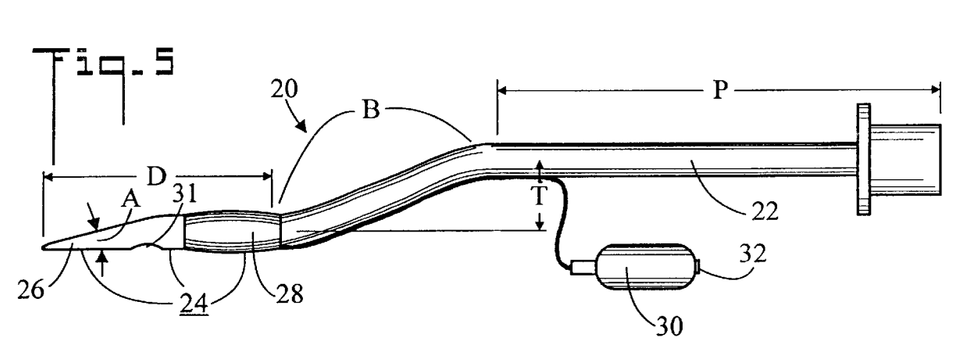
FIG. 5 is a side elevation view of an endotracheal tube for an animal in accordance with the present invention.
Figure 6:
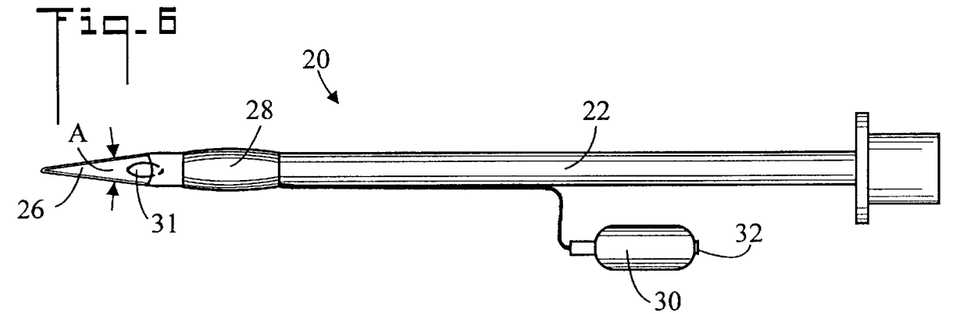
FIG. 6 is a top plan view of the endotracheal tube.
Figure 7:
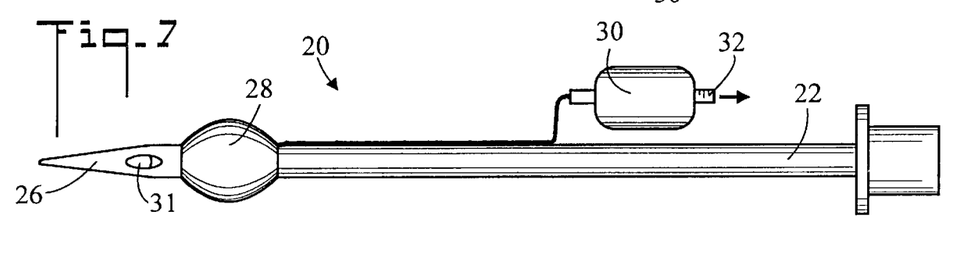
FIG. 7 is a bottom plan view of the endotracheal tube.

FIGS. 5–7 illustrate side elevation, top plan, and bottom plan views, respectively, of an endotracheal tube for an animal in accordance with the present invention, generally designated as 20. Endotracheal tube 20 has an elongated firm body 22 having a proximal portion P and a distal portion D. A double bend B is disposed in body 22 between proximal P and distal D portions. A double bend B is defined herein as an angular bend in one direction and then an approximately equal angular bend in an opposite direction, so that distal portion D is transversely displaced a distance T with respect to proximal portion P. In other words, proximal portion P is longitudinally oriented in a direction, endotracheal tube 20 then bends at an angle and then bends back at an approximate equal angle, so that distal portion D is longitudinally oriented in approximately the same direction as proximal portion P. Distal portion D has an outward facing surface 24 for depressing the epiglottis 606 of the animal (refer also to FIG. 8). Outward facing surface 24 is the surface transversely furthest from proximal portion P.

Figure 9:
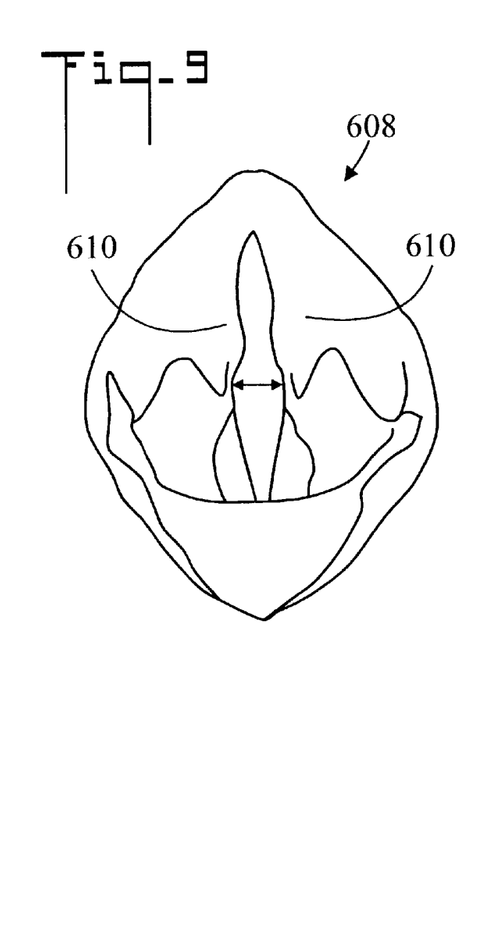
FIG. 9 is an enlarged front elevation view of the larynx of an animal.
Figure 10:
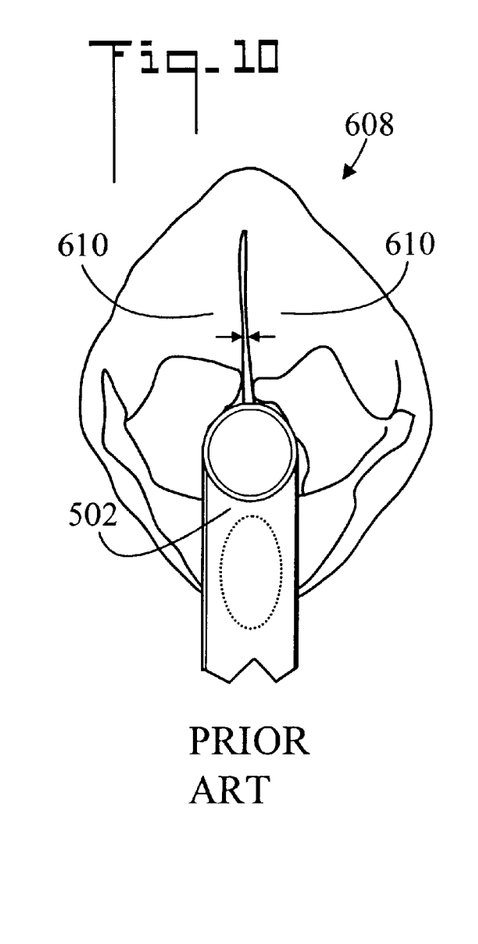
FIG. 10 is an enlarged front elevation view of the larynx of an animal fully closed and the blunt tip of the prior art human endotracheal tube.
Figure 11:
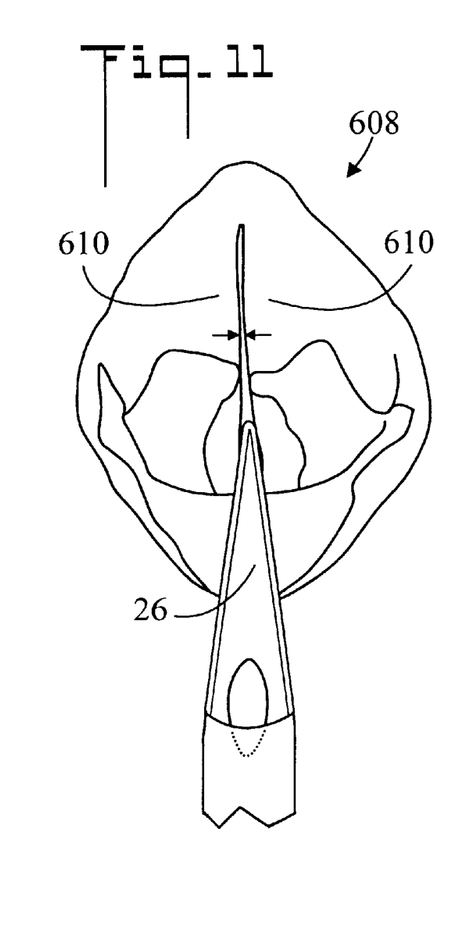
FIG. 11 is an enlarged front elevation view of the larynx of an animal fully closed and the tapered end of the present invention.

Distal portion D has a tapered end 26 for passing endotracheal tube 20 through the arytenoid cartilages and into the trachea 606 of the animal (refer also to FIGS. 9–11). As used herein, a tapered end means an end that tapers down in all directions such as that of a sharpened pencil. In order to easily pass though the arytenoid cartilages of the larynx, tapered end 26 forms an angle A which is less than 25°. This is in contrast to the blunt tip 502 of a human endotracheal tube, which is difficult to pass into the trachea 602 of an animal. As with human endotracheal tubes 500, a Murphy's eye 31 is disposed in tapered end 26.

Endotracheal tube 20 also has an inflatable cuff 28 which is shown uninflated in FIGS. 5 and 6 and inflated in FIG. 7. A pilot balloon 30 is connected to inflatable cuff 28. Pilot balloon 30 includes a pressure indicator 32 for measuring air pressure within cuff 28. Pressure indicator 32 provides the doctor with a quantitative indication of the air pressure within cuff 28. In the shown embodiment, pressure indicator 32 includes a calibrated plunger which is forced outward a distance proportional to the air pressure within cuff 28.

Figure 8:
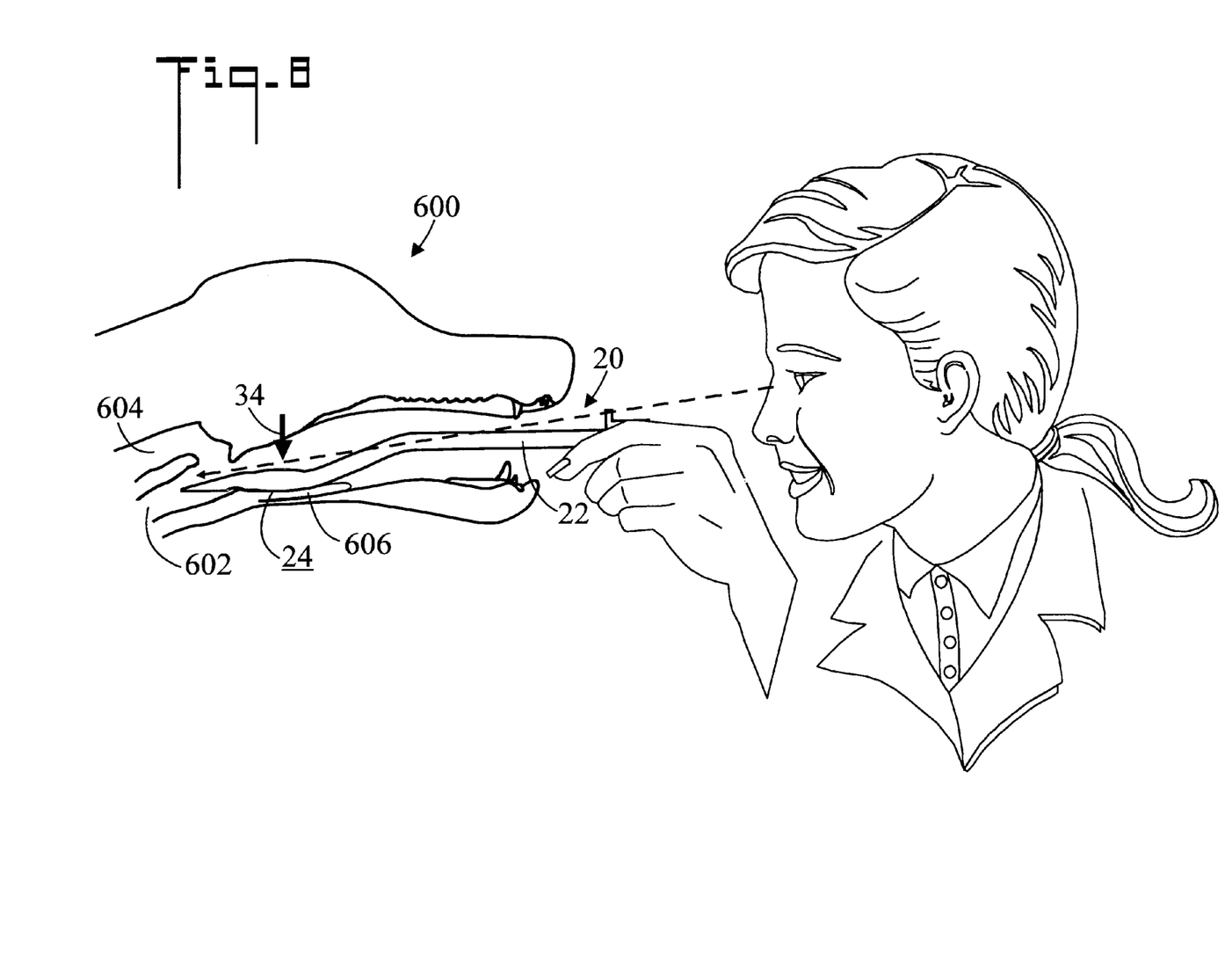
FIG. 8 is a reduced side elevation view of the endotracheal tube being inserted into the mouth of an animal.

FIG. 8 is a reduced side elevation view of endotracheal tube 20 being inserted into the mouth of an animal 600. Outward facing surface 24 is used to depress the epiglottis 606 so that the doctor has an unobstructed view of the animal's trachea 602. The bends B in endotracheal tube 20 make this procedure possible (refer also to FIG. 5). It is important that endotracheal tube 20 have a firm body 22 so that pressure may be exerted in direction 34 to depress epiglottis 606. Conventional human endotracheal tubes 500 are made from flexible materials which could not be used to perform the depressing action of the present invention.

FIG. 9 is an enlarged front elevation view of the larynx 608 of an animal. The larynx 608 is shown with the arytenoid cartilages 610 in a partially open position.

FIG. 10 is an enlarged front elevation view of the larynx 608 of an animal and the prior art blunt tip 502 of a human endotracheal tube 500. The arytenoid cartilages 610 are fully closed in laryngospasm. It is noted that blunt tip 502 cannot easily pass between the arytenoid cartilages 610 and into the trachea 602.

FIG. 11 is an enlarged front elevation view of the larynx 608 of an animal and the tapered end 26 of endotracheal tube 20. The arytenoid cartilages 610 are fully closed in laryngospasm. It is noted that tapered end 26 is small enough to pass between the arytenoid cartilages 610 and into the trachea 602 allowing the body of endotracheal tube to follow by wedging the arytenoid cartilages apart.

Figure 12:
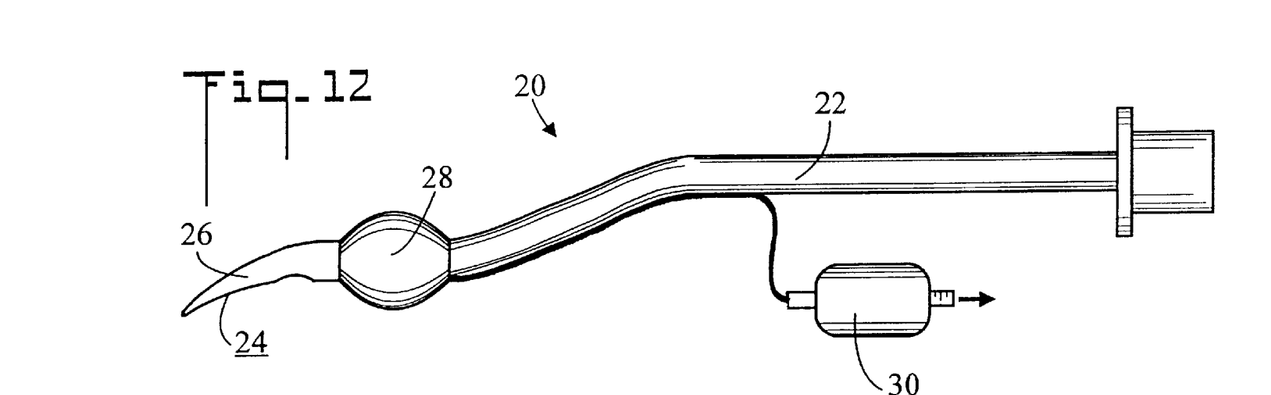
FIG. 12 is a side elevation view of a second embodiment of the endotracheal tube.

FIG. 12 is a side elevation view of a second embodiment of endotracheal tube 20. In this embodiment tapered end 26 is curved toward outward facing surface 24.

Figure 13:
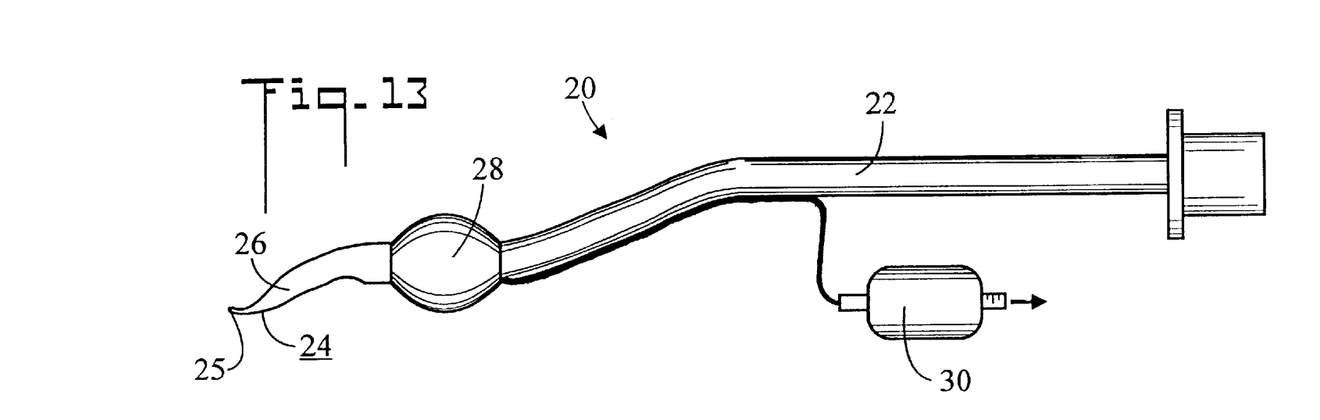
FIG. 13 is a side elevation view of a third embodiment of the endotracheal tube.

FIG. 13 is a side elevation view of a third embodiment of endotracheal tube 20. In this embodiment tapered end 26 is curved toward outward facing surface 24, and also has a tip 25 which curves away from outward facing surface 24.

Figure 14A:
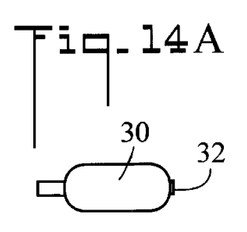
FIG. 14A is a side elevation view of a first embodiment of a pilot balloon in an uninflated state.

FIG. 14A is a side elevation view of a first embodiment of a pilot balloon 30 in an uninflated state. Pressure indicator 32 includes a calibrated plunger similar to the plunger on a tire pressure gauge.

Figure 14B:
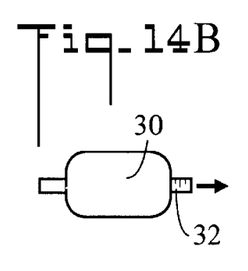
FIG. 14B is a side elevation view of the first embodiment of the pilot balloon in an inflated state.

FIG. 14B is a side elevation view of the first embodiment of the pilot balloon 30 in an inflated state. The plunger has been forced outward a distance proportional to the air pressure within cuff 28, thereby giving the doctor a quantitative measure of air pressure within cuff 28.

Figure 15A:
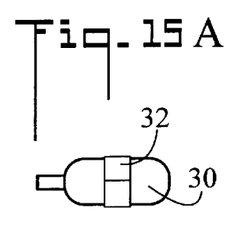
FIG. 15A is a side elevation view of a second embodiment of a pilot balloon in an uninflated state.

FIG. 15A is a side elevation view of a second embodiment of a pilot balloon 30 in an uninflated state. Pressure indicator 32 includes a calibrated band placed around pilot balloon 30.

Figure 15B:
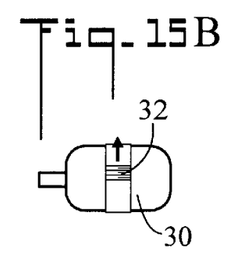
FIG. 15B is a side elevation view of the second embodiment of the pilot balloon in an inflated state.

FIG. 15B is a side elevation view of the second embodiment of the pilot balloon 30 in an inflated state. Pilot balloon 30 has circumferentially expanded as a function of the air pressure within cuff 28, thereby giving the doctor a quantitative measure of air pressure within cuff 28.

Figure 16A:
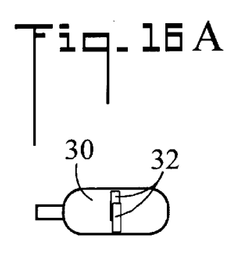
FIG. 16A is a side elevation view of a third embodiment of a pilot balloon in an uninflated state.

FIG. 16A is a side elevation view of a third embodiment of a pilot balloon 30 in an uninflated state. Pressure indicator 32 includes two strips disposed on a surface of pilot balloon 30.

Figure 16B:
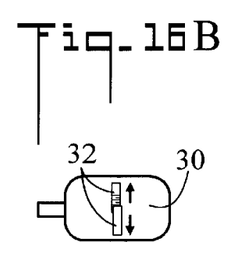
FIG. 16B is a side elevation view of the third embodiment of the pilot balloon in an inflated state.

FIG. 16B is a side elevation view of the third embodiment of the pilot balloon 30 in an inflated state. The longitudinal relationship of the strips changes as a function of the air pressure within cuff 28. A calibrated scale on one of the strips provides the doctor with a quantitative measure of air pressure within cuff 28.

Figure 17A:
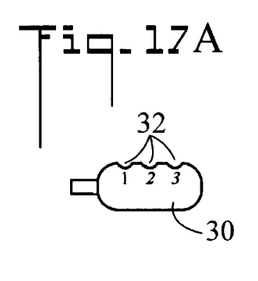
FIG. 17A is a side elevation view of a fourth embodiment of a pilot balloon in an uninflated state.

FIG. 17A is a side elevation view of a fourth embodiment of the pilot balloon 30 in an uninflated state. A plurality of dimples are disposed on a surface of pilot balloon 30. Each dimple pops out when a different threshold pressure is reached within cuff 28. For example a first dimple might pop out at 10 cm of water, a second dimple might pop out at 15 cm of water, and a third dimple might pop out at 20 cm of water. The different pressure thresholds are obtained by varying the thicknesses of the walls of the dimples.

Figure 17B:
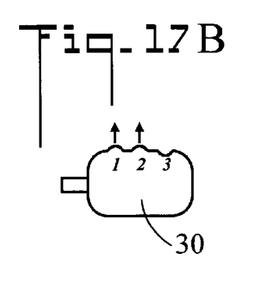
FIG. 17B is a side elevation view of the fourth embodiment of the pilot balloon in an inflated state.

FIG. 17B is a side elevation view of the fourth embodiment of the pilot balloon 30 in an inflated state. The air pressure within cuff 28 is between 15 cm and 20 cm. Therefore, the 10 cm and 15 cm dimples have popped out.

Figure 18A:
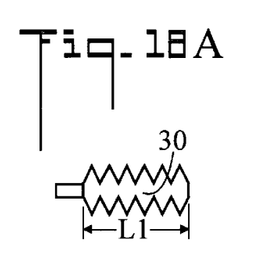
FIG. 18A is a side elevation view of a fifth embodiment of a pilot balloon in an uninflated state.

FIG. 18A is a side elevation view of a fifth embodiment of the pilot balloon 30 in an uninflated state. Pilot balloon 30 is formed in the shape of a bellows having a length L1.

Figure 18B:
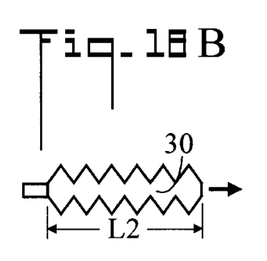
FIG. 18B is a side elevation view of the fifth embodiment of the pilot balloon in an inflated state.

FIG. 18B is a side elevation view of the fifth embodiment of the pilot balloon 30 in an inflated state. The length of the bellows has increased to L2 as a function of the air pressure within cuff 28. The increase in length gives the doctor a quantitative measure of air pressure within cuff 28.

Figure 19A:
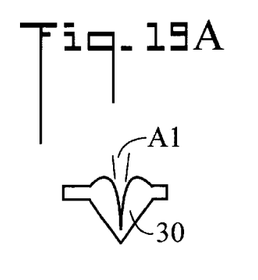
FIG. 19A is a side elevation view of a sixth embodiment of a pilot balloon in an uninflated state; and, FIG. 19B is a side elevation view of the sixth embodiment of the pilot balloon in an inflated state.

FIG. 19A is a side elevation view of a sixth embodiment of a pilot balloon 30 in an inflated state. Pilot balloon 30 includes first and second portions which form an angle A1 therebetween.

Figure 19B:
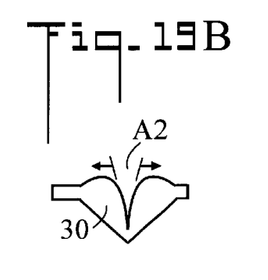

FIG. 19B is a side elevation view of the sixth embodiment of the pilot balloon 30 in an inflated state. The angle has increased to A2 as a function of the air pressure within cuff 28. The angular increase gives the doctor a quantitative measure of air pressure within cuff 28.

In terms of use, a method for performing tracheal intubation on an animal 600, includes:

(a) providing an animal 600 having a mouth and an epiglottis 606;

(b) providing an endotracheal tube 20 having:
an elongated firm body 22 having a proximal portion P and a distal portion D;
a double bend B disposed in body 22 between the proximal P and distal D portions, so that the distal portion D is transversely displaced with respect to proximal portion P; and,
distal portion D having an outward facing surface 24 for depressing the epiglottis 606 of the animal 600;

(c) inserting the distal end D of endotracheal tube 22 into the mouth of the animal 600; and, (d) using the outward facing surface 24 to depress the epiglottis 606 of the animal 600.

Another method for performing tracheal intubation on an animal 600 includes:

(a) providing an animal 600 having a larynx 608 having arytenoid cartilages 610 and a trachea 602;

(b) providing an endotracheal tube 20 including:
an elongated body 22 having a proximal portion P and a distal portion D;
distal portion D having a tapered end 26 for passing the endotracheal tube 20 through the arytenoid cartilages 610 and into the trachea 602; and,
tapered end 26 forming an angle A which is less than 25°;

(c) using the tapered end 26 to pass endotracheal tube 20 through the arytenoid cartilages 610 and into the trachea 602 of the animal 600.

Another method for performing tracheal intubation on an animal 600 includes:

(a) providing an animal 600 having a trachea 602;

(b) providing an endotracheal tube 20 including:
an inflatable cuff 28;
a pilot balloon 30 connected to cuff 28; and,
pilot balloon 30 including a pressure indicator 32 for measuring air pressure within cuff 28;

(c) inserting cuff 28 into the trachea 602 of animal 600;

(d) inflating inflatable cuff 28; and, (h) using pressure indicator 32 to measure air pressure within cuff 28.

It will be appreciated that many of the features provided by the endotracheal tube of the present invention for use on a small animal can also be applied to an endotracheal tube for use on a human. Specifically, an endotracheal tube angled in a zigzag fashion may be used to depress the epiglottis of a human while providing better visibility. A tapered end on a tube may be provided to facilitate the insertion of the tube in a human. And, a more accurate quantitative pressure sensor may be provided on a tube for use on a human to better control the over or under inflation of the inflatable cuff.

The preferred embodiments of the invention described herein are exemplary and numerous modifications, variations, and rearrangements can be readily envisioned to achieve an equivalent result, all of which are intended to be embraced within the scope of the appended claims.

I claim:

1. A method for performing tracheal intubation on an animal, comprising:

(a) providing an animal having a mouth and an epiglottis;

(b) providing an endotracheal tube having:
an elongated firm body having a straight proximal portion and straight distal portion;
a double bend disposed in said body between said proximal and distal portions having an angular bend in one direction and then an approximately equal angular bend in an opposite direction, so that said distal portion is transversely displaced with respect to said proximal portion with said distal portion longitudinally oriented in approximately the same direction as said proximal portion; and,
said distal portion having an outward facing surface for depressing said epiglottis of said animal;

(c) inserting said distal end of said endotracheal tube into said mouth of said animal;

(d) viewing along said proximal portion to said angular bend, said distal portion, and said epiglottis; and, (e) using said outward facing surface to depress said epiglottis of said animal.

2. The method of claim 1, further including:
in step (a), said animal having a larynx having arytenoid cartilages and a trachea;
in step (b), said distal portion having a tapered end for passing said endotracheal tube through said arytenoid cartilages and into said trachea, said tapered end forming an angle which is less than 25°; and, (f) using said tapered end to pass said endotracheal tube through said arytenoid cartilages and into said trachea.

3. The method of claim 2, further including:
in step (b), said endotracheal tube having:
an inflatable cuff;
a pilot balloon connected to said cuff; and,
said pilot balloon including a pressure indicator for measuring air pressure within said cuff;

(g) inserting said inflatable cuff into said trachea of said animal;

(h) inflating said inflatable cuff; and, (i) using said pressure indicator to measure air pressure within said cuff.

4. A method for performing tracheal intubation on an animal, comprising;

(a) providing an animal having a trachea;

(b) providing an endotracheal tube including:
an inflatable cuff;
a pilot balloon connected to said cuff; and,
said pilot balloon including a pressure indicator having a plurality of dimples on a surface for measuring air pressure within said cuff, each dimple popping out when a different threshold pressure is reached within said cuff;

(c) inserting said cuff into said trachea of said animal;

(d) inflating said inflatable cuff; and, (e) using said pressure indicator to measure air pressure within said cuff.

5. An endotracheal tube for an animal having an epiglottis, said endotracheal tube comprising:
an elongated firm body having a straight proximal portion and straight distal portion;
a double bend disposed in said body between said proximal and distal portions having an angular bend in one direction and then an approximately equal angular bend in an opposite direction, so that said distal portion is transversely displaced with respect to said proximal portion with said distal portion longitudinally oriented in approximately the same direction as said proximal portion; and, said distal portion having an outward facing surface for depressing the epiglottis of the animal.

6. An endotracheal tube according to claim 5, the animal having a larynx having arytenoid cartilages and a trachea, said endotracheal tube further including:

said distal portion having a tapered end for passing said endotracheal tube through the arytenoid cartilages and into the trachea; and, said tapered end forming an angle which is less than 25°.

7. An endotracheal tube according to claim 5, further including:

said endotracheal tube having an inflatable cuff;

a pilot balloon connected to said cuff; and, said pilot balloon including a pressure indicator for measuring air pressure within said cuff.

8. An endotracheal tube for an animal, comprising:

an inflatable cuff;

a pilot balloon connected to said cuff; and, said pilot balloon including a pressure indicator having a plurality of dimples on a surface for measuring air pressure within said cuff, each dimple popping out when a different threshold pressure is reached within said cuff.

9. An endotracheal tube according to claim 8, the animal having an epiglottis, said endotracheal tube further including:

an elongated firm body having a proximal portion and a distal portion;

a double bend disposed in said body between said proximal and distal portions, so that said distal portion is transversely displaced with respect to said proximal portion; and, said distal portion having an outward facing surface for depressing the epiglottis of the animal.

10. An endotracheal tube according to claim 8, the animal having a larynx having arytenoid cartilages and a trachea, said endotracheal tube further including:

said distal portion having a tapered end for passing said endotracheal tube through the arytenoid cartilages and into the trachea; and, said tapered end forming an angle which is less than 25°.

* * * * *